US007563018B2

(12) United States Patent  (10) Patent No.: US 7,563,018 B2
Wilander  (45) Date of Patent: Jul. 21, 2009

(54) DEVICE FOR PRODUCING BONE CEMENT AND METHOD IN CONNECTION THEREWITH

(75) Inventor: Lars Wilander, Orkelljunga (SE)

(73) Assignee: Biomet Cementing Technologies AG, Sjobo (SE)

( * ) Notice: Subject to any disclaimer, the term of this patent is extended or adjusted under 35 U.S.C. 154(b) by 195 days.

(21) Appl. No.: 11/118,913

(22) Filed: Apr. 29, 2005

(65) Prior Publication Data

US 2006/0109737 A1  May 25, 2006

(30) Foreign Application Priority Data

Nov. 24, 2004 (SE) .................................... 0402856

(51) Int. Cl.
*B01F 13/06* (2006.01)
(52) U.S. Cl. ....................................... 366/139; 366/189
(58) Field of Classification Search ................. 366/139, 366/189; 222/389
See application file for complete search history.

(56) References Cited

U.S. PATENT DOCUMENTS

| 195,126 | A | * | 9/1877 | Hersey ........................ 222/389 |
| 716,910 | A | * | 12/1902 | Lubbecke .................... 222/129 |
| 765,134 | A | * | 7/1904 | Freeman ..................... 222/389 |
| 923,550 | A | * | 6/1909 | Mikorey ..................... 222/389 |
| 938,084 | A | * | 10/1909 | Stout ........................... 222/387 |
| 4,185,072 | A | * | 1/1980 | Puderbaugh et al. .......... 422/99 |
| 4,721,390 | A | * | 1/1988 | Lidgren ...................... 366/139 |
| 5,328,262 | A | | 7/1994 | Lidgren et al. |
| 5,788,463 | A | | 8/1998 | Chan |
| 2002/0191484 | A1 | | 12/2002 | Jonsson |
| 2002/0191485 | A1 | | 12/2002 | Jonsson |

FOREIGN PATENT DOCUMENTS

EP  0 768 067 A2  4/1997

* cited by examiner

*Primary Examiner*—David L Sorkin
(74) *Attorney, Agent, or Firm*—Tarolli, Sundheim, Covell & Tummino LLP

(57) ABSTRACT

The present invention relates to a mixing device for producing bone cement by mixing components intended therefor, wherein the bone cement (3) is made by mixing the components (4, 5) under a vacuum in a mixing space (6), and wherein the mixing space (6) includes at least one piston (9) which can be brought to remain in a start position (A) during mixing and which is releasable therefrom after mixing, whereby said piston (9) will be sucked into the mixing space (6) by being affected by the vacuum prevailing therein. At least one throttle device (20) is provided for generating a pressure drop between the air pressure in the surroundings and the piston (9) for preventing full power affection thereof by said air pressure. At a method in connection with said device, the piston (9) is brought to remain in the start position (A) during mixing of the components (4, 5) by air-tight isolation thereof from the surroundings. The piston (9) can be released from the start position (A) by opening the air-tight isolation.

19 Claims, 5 Drawing Sheets

DEVICE FOR PRODUCING BONE CEMENT AND METHOD IN CONNECTION THEREWITH

FIELD OF THE INVENTION

The present invention relates to a device for producing bone cement by mixing components adapted therefor. The bone cement is made by mixing the components under a vacuum in a mixing space. This mixing space includes at least one piston which can be brought to remain in a start position during mixing and which is releasable therefrom after mixing, whereby said piston will be sucked into the mixing space by being affected by the vacuum prevailing therein. The invention also relates to a method in connection with the production of bone cement.

BACKGROUND OF THE INVENTION

The publication U.S. Pat. No. 5,328,262 (SE 510490) describes the advantages by mixing and collecting bone cement under a vacuum. The object thereof is to reduce the porosity of the bone cement in order to impart important properties thereto.

A condition for arriving at this object is that a sufficient vacuum is generated in the mixing space. The mixing space is dimensioned for producing a certain amount of bone cement and when the piston is released, it is displaced up into the mixing space at a reasonable speed due to the difference between the pressures inside and outside the mixing space and the area of the piston.

However, it has been noticed that if the mixing space is dimensioned for producing larger amounts of bone cement and if the area of the piston thereby increases, the speed of the piston may be so high that problems arise.

SUMMARY OF THE INVENTION

The object of the present invention is to eliminate these problems by simple means. This is arrived at by providing the invention with the characterizing features of subsequent claims 1 and 26.

By means of a throttle device, the atmospheric air pressure is prevented from affecting the piston with full power when said piston is released and it is thereby prevented that the piston can be accelerated to unsuitably high speeds.

BRIEF DESCRIPTION OF THE DRAWINGS

The invention will be further described below with reference to the accompanying drawings, in which.

DESCRIPTION OF EXAMPLE EMBODIMENTS

Figure 1:
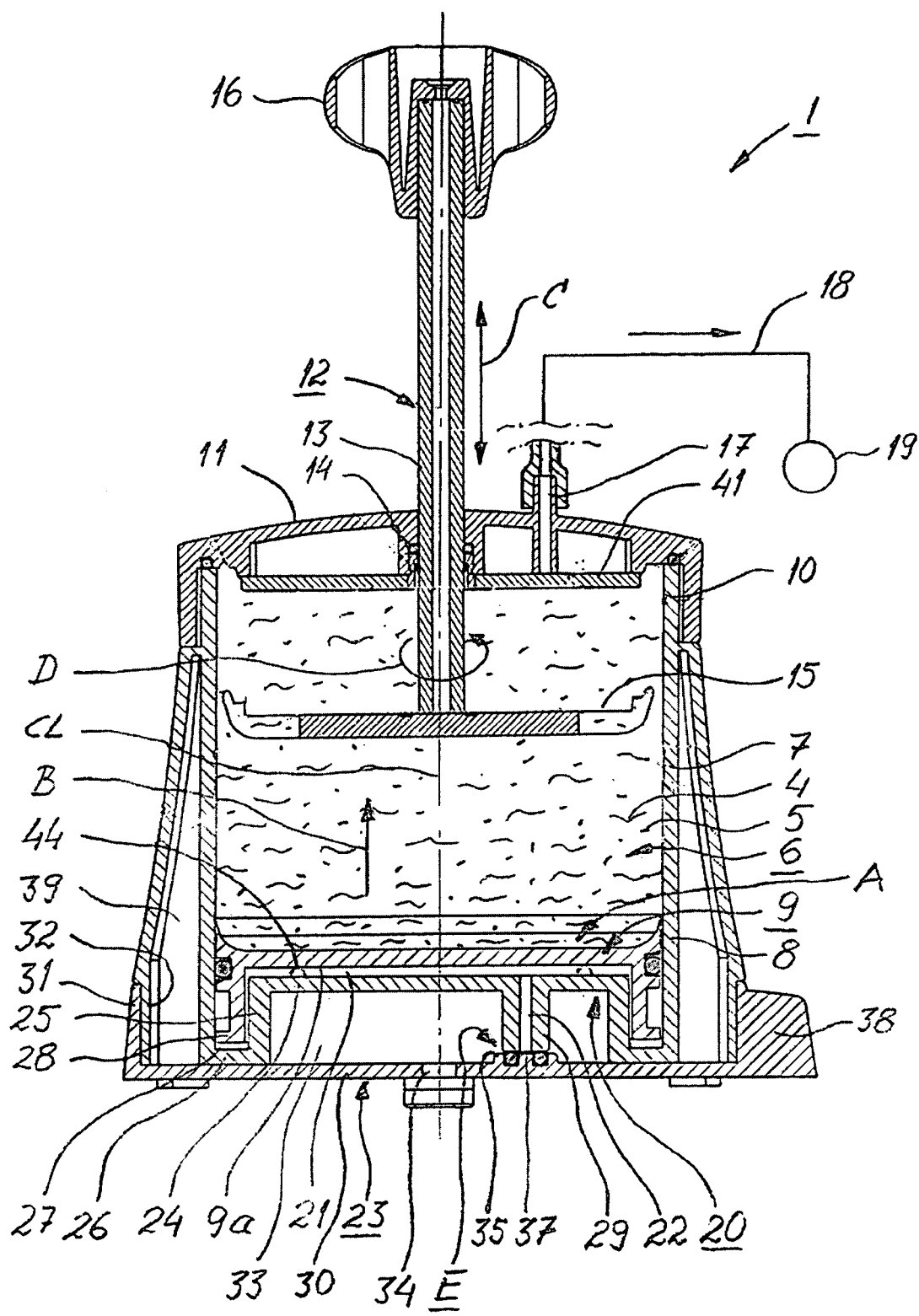
FIG. 1 is a section through a mixing device during mixing of bone cement and with a device according to the invention.
Figure 2:
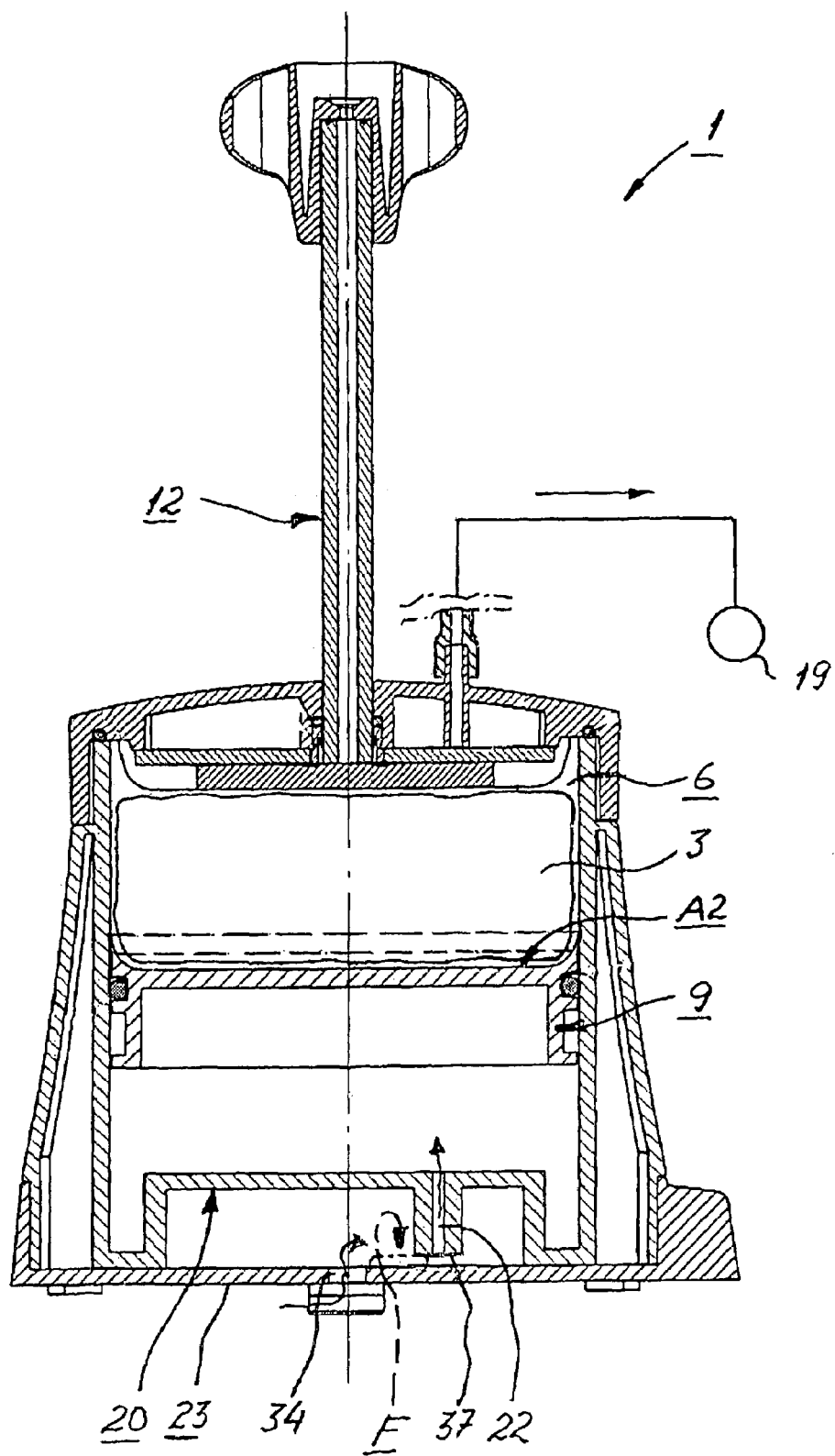
FIG. 2 is a section through the mixing device of FIG. 1 after mixing of bone cement therein, after release of the piston and after movement or displacement of the piston and collection of the bone cement.
Figure 3:
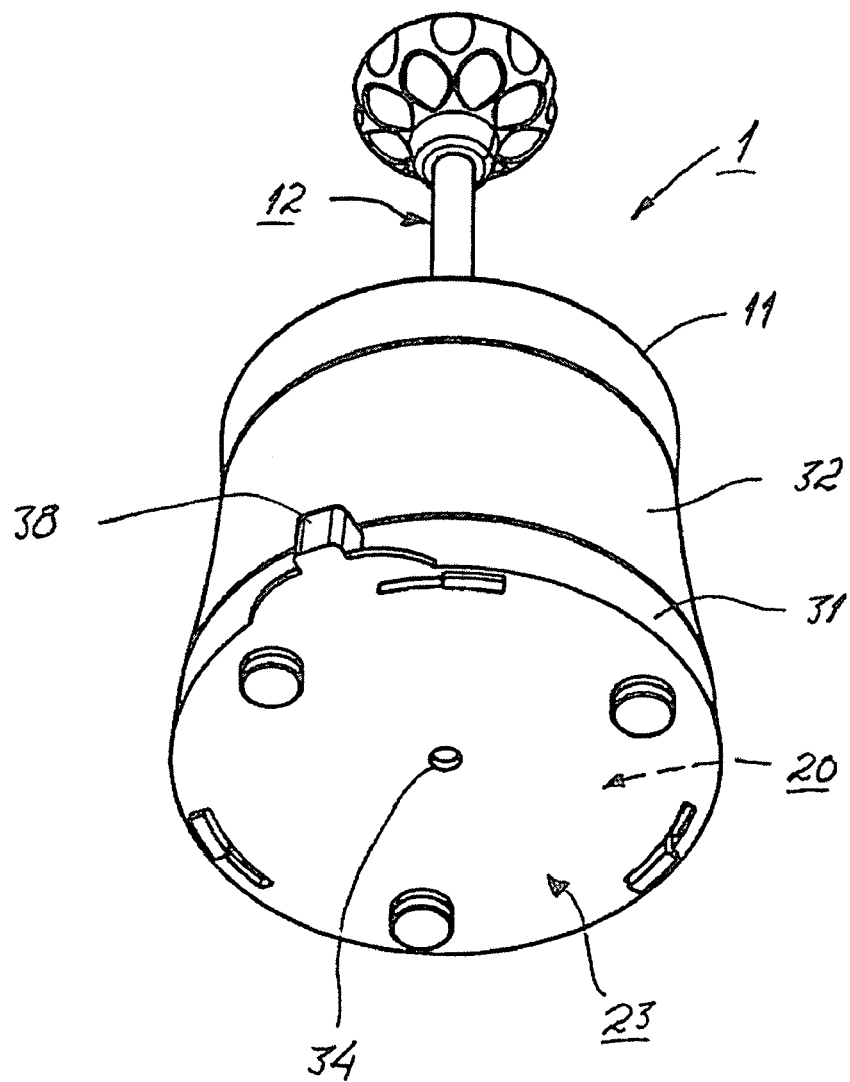
FIG. 3 is a perspective view of the mixing device of FIG. 1.
Figure 4:
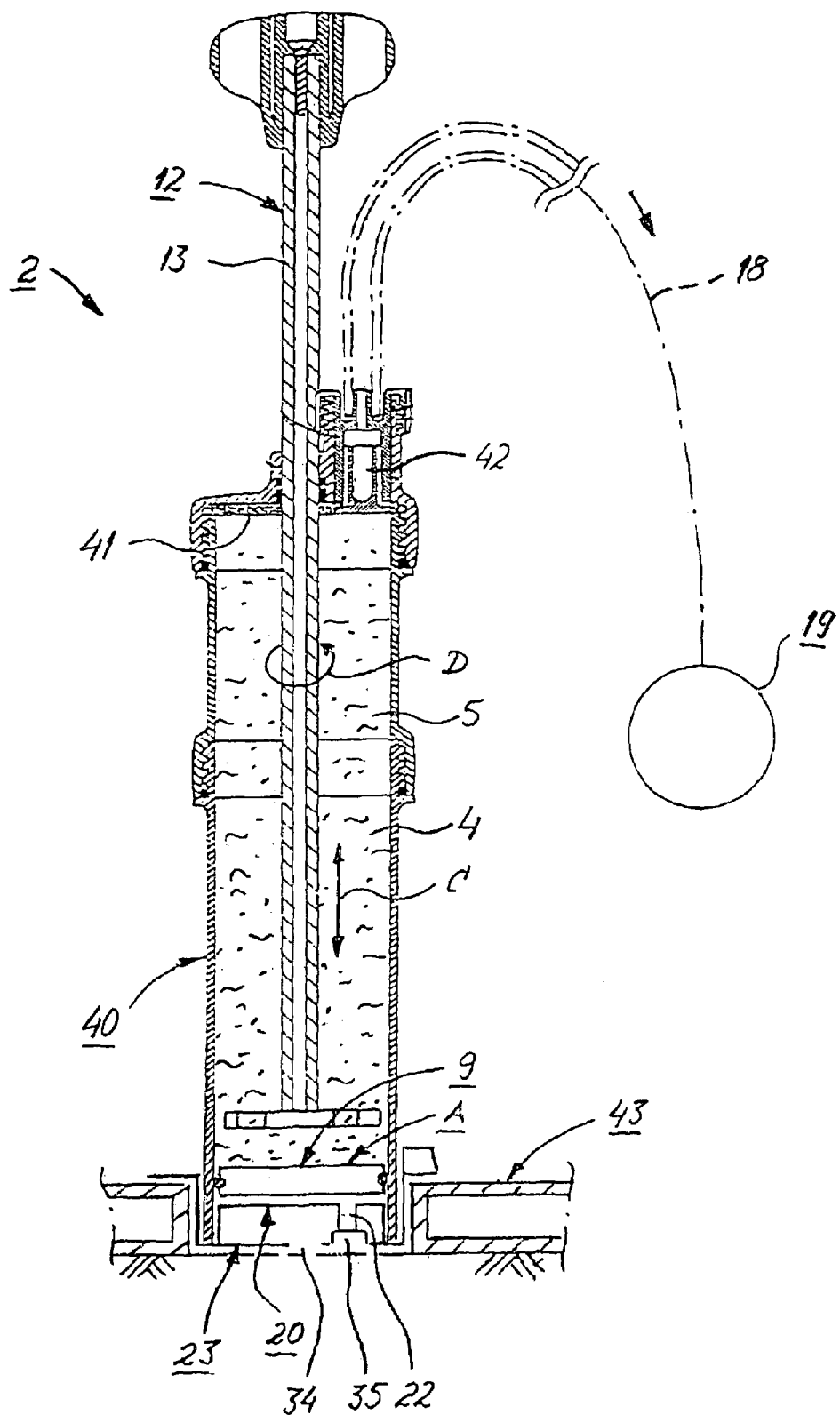
FIG. 4 is a section through another mixing device during mixing of bone cement and with a device according to the invention.
Figure 5:
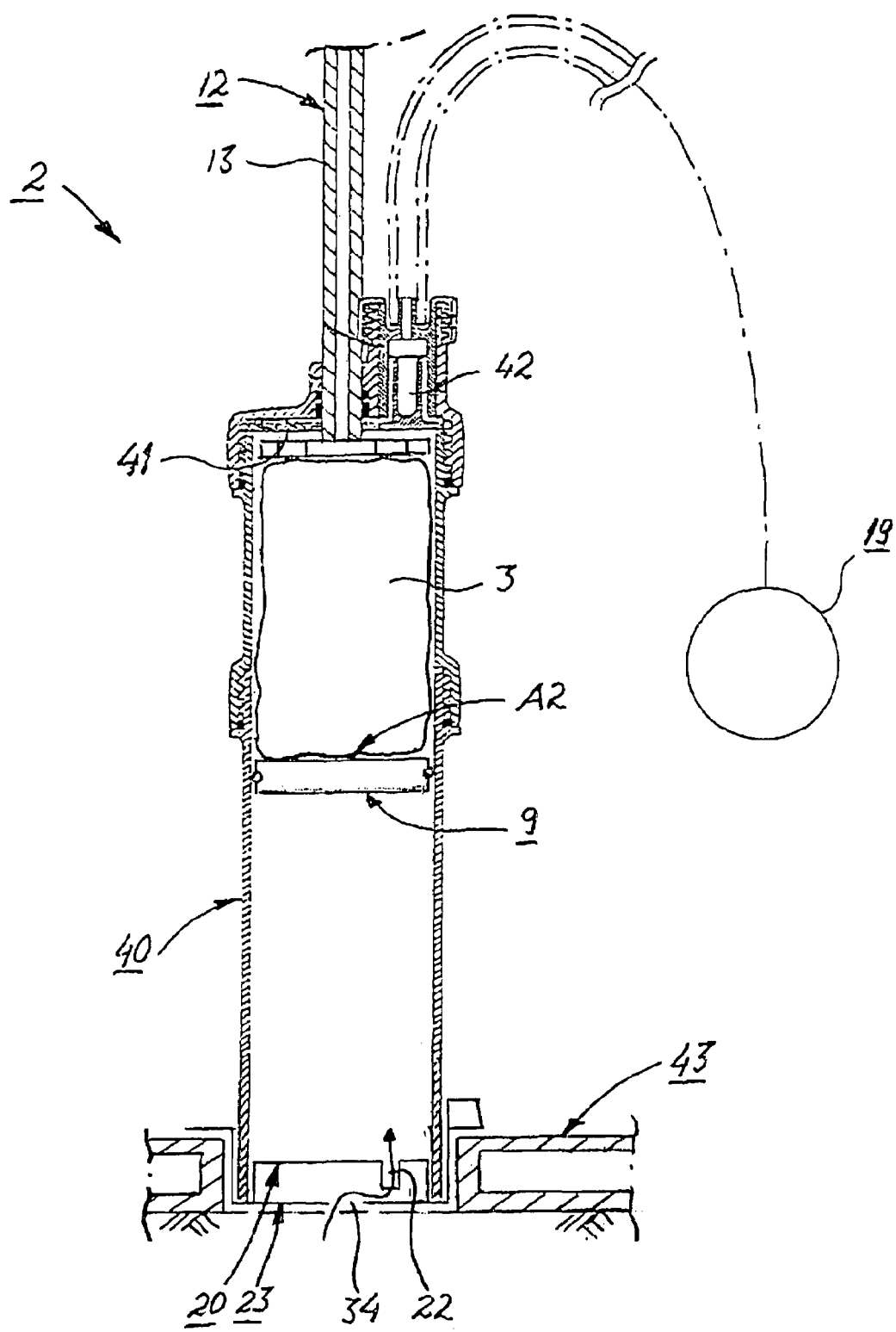
FIG. 5 is a section through the mixing device of FIG. 4 after mixing of bone cement therein, after location of the mixing device for cooperation with a device according to the invention, after release of a piston and after movement or displacement of the piston and collection of bone cement.

The mixing device 1 illustrated in FIGS. 1-3 and the mixing device shown in FIGS. 4 and 5 are adapted for producing bone cement 3 by mixing two or more components 4, 5, preferably monomer 4 and polymer 5. Such bone cement is used, inter alia, for fastening prostheses to the bones of the body.

The mixing device 1 is adapted to be opened at the top after mixing, whereupon the mixed bone cement 3 is removed from the mixing device by means of a spoon-like instrument and then applied at the desired location in a bone for fastening a an implant thereto.

The mixing device 1 has a mixing space 6 which at the illustrated embodiment is defined by cylindrical walls 7. The mixing space 6 is at a first end portion 8—e.g. a lower end portion—closed by means of a piston 9 and is at a second end portion 10—e.g. an upper end portion—closed by means of a removable cap 11. The piston 9 sealingly engages the inner sides of the walls 7, preferably through sealing elements, and it can be moved or displaced from a start position A at or adjacent to the first end portion 8 in an axial direction B towards the second end portion 10, namely an axial direction B relative to a geometric centre line CL for the cylindrical walls 7 of the mixing space 6.

The mixing device 1 also includes a mixing means 12 for mixing the components 4, 5 in the mixing space 6. At the illustrated embodiment, the mixing means 12 comprises a rod 13 which extends displaceably through the cap 11 into the mixing space 6 and engages said cap 11 sealingly by cooperating with at least one sealing means 14 provided in said cap.

In the mixing space 6, the rod 13 has a mixing element 15 of a suitable shape and its outer end portion has outside the mixing space 6 a handle 16 of a suitable shape.

For mixing the components 4, 5 in the mixing space 6, the mixing means 12 is movable by hand in axial directions C up and down in the mixing space 6 and also rotatable in relation thereto according to arrow D. At the illustrated embodiment, the mixing means 12 is preferably operated by hand.

The cap 11 has a tube member 17 for connection of a hose 18 or similar which is adapted for connecting the mixing space 6 with a vacuum source 19, e.g. a vacuum pump. The vacuum pump is adapted for generating a vacuum in the mixing space 6 during the mixing operation and preferably also during a subsequent collecting operation.

In the cap 11 or at another suitable location there is preferably provided a filter 41 which is adapted for preventing holes in the tube member 17 and/or other suction passages in the mixing device 1 from being obstructed by bone cement 3 when the vacuum source generates a vacuum in the mixing space 6.

The bone cement to be produced may be of Palacos® type or of another suitable type and it may be, although not necessarily, of high viscosity. The vacuum source 19 may be a vacuum pump of Scandimed® type or another suitable type and the vacuum generated in the mixing space may preferably be about 0.05 bar or lie within in a range of 0.1-0.03 bar.

For producing the bone cement 3 in the mixing space 6, the monomer component 4 and the powder polymer component 5 are poured into said mixing space. Then, the cap 11 is located thereon and fastened with screws or in another suitable way to the cylindrical walls 7. The vacuum source 19 is activated or has been activated for generating said vacuum in the mixing space 6. For mixing the components 4, 5 under a vacuum, the mixing means 12 is moved up and down a number of times and is at the same time preferably rotated. When mixing is finished, the piston 9 is released and said piston is thereby moved or displaced in the axial direction B under the influence of the air pressure outside the mixing space 6, i.e. by the atmospheric air pressure, and while the air pressure is higher than the vacuum prevailing in said mixing space.

During said movement or displacement upwards in the axial direction B, the piston 9 collects the mixed bone cement 3—inter alia such mixed bone cement 3 which during mixing has been deposited on the inner sides of the cylindrical walls 7—at the second end portion 10 of the mixing space 6. Preferably, the piston 9 collects all bone cement 3 that is mixed and ready at the second end portion 10, and by maintaining during the collection the vacuum already prevailing during the mixing operation, it is achieved that the collected bone cement is free from or substantially free from entrapped air.

When the bone cement 3 has been collected at the second end portion 10 of the mixing space 6, the vacuum generation is concluded by closing the vacuum source 19 and/or by loosening the hose 18 from the tube member 17 on the cap 11. The cap 11 is removed and bone cement 3 is removed from the mixing space 6 e.g. as previously described.

A throttle device 20 is provided to generate a pressure drop between the ambient air pressure, i.e. the atmospheric air pressure, and the piston 9 in order to prevent this air pressure from affecting the piston 9 with full power when said piston is released. Hereby, it is prevented that such an unpropitious high speed is imparted to the piston 9 after its release that said piston can be damaged and/or damage members of the mixing device 1 and/or negatively affect the quality of the bone cement 3.

The throttle device 20 can be designed in many different ways in order to fulfill the abovementioned objects and it may, but does not necessarily, be located on the mixing device 1.

Thus, at the mixing device 1 illustrated in FIGS. 1-3, the throttle device 20 is provided on the mixing device 1 itself and it can with the piston 9 define an intermediate space 21. The throttle device 20 preferably has at least one hole 22 through which the intermediate space 21 can communicate with the surroundings. The least cross-sectional area of the hole 22 (or all the least cross-sectional areas of the holes) is at the illustrated embodiment less than the area of the outer side 9a of the piston 9 which is facing the intermediate space 21 and determines the pressure drop which is momentarily generated and thereby, the force by means of which the air pressure momentarily can affect the piston 9.

The mixing device 1 preferably also comprises a closing device 23 which in cooperation with the throttle device 20 can be brought to close the hole 22 or holes therein and thereby isolate the piston 9 from the surroundings and in this way prevent the air from flowing into the intermediate space 21. By isolating the piston 9 from the surroundings, it is prevented from being sucked into the mixing space 6 by a vacuum prevailing therein during mixing of the components 4, 5 or at least prevented from being sucked up a substantial distance.

When the piston 9 has been sucked to an inner position A2 after collection of the bone cement 3, the throttle device 20 can be closed by the closing device 23 such that the piston 9 can be brought to remain therein by once again isolating it from the surroundings.

The hole 22 or holes can be closed by changing the relative positions of the throttle device 20 and the closing device 23.

The hole 22 or holes can be completely or partly opened in dependence of how large a pressure drop one desires momentarily, i.e. at which speed one wishes the piston 9 to move. This can be done by selecting a certain extent of the relative movement between the throttle and closing devices 20, 23 and/or by designing the hole 22 or holes in a particular way in view thereof.

The closing device 23 may e.g. be movable relative to the throttle device 20 for closing the hole 22 or holes in said latter device.

At the embodiment illustrated in FIGS. 1-3, the closing device 23 is also located on the mixing device 1 itself. The throttle device 20 can e.g. include a wall-like member 24 which is rigidly connected with or in any other way provided on a lower end portion of the cylindrical walls 7, such that it with the exception of the hole 22 closes the mixing space 6 down below. The wall-like member 24 can e.g. include an outer annular wall portion 25 which extends in an axial direction relative to the cylindrical walls 7 and which through a radially directed wall portion 26 can be connected therewith. The wall portions 25, 26 can with the cylindrical walls 7 define a space 27 into which parts 28 of the piston 9 may extend.

The wall-like member 24 includes e.g. a tube member 29 which is directed towards the closing device 23, is provided with the hole 22 and is eccentrically mounted relative to the centre line CL. The closing device 23 can have a wall 30 with an axially directed annular flange 31. This flange is e.g. pivotally or rotatably mounted on cylindrical outer walls 32 which surround parts of the cylindrical walls 7. The wall 30 defines with the wall-like member 24 an outer space 33 and it has at least one hole 34 through which the outer space 33 communicates with the surroundings. The hole 34 can be centered or substantially centered with the centre line CL.

The wall 30 may on the inner side have a closing portion 35 which is e.g. raised and has a sealing ring 36. This closing portion 35 is eccentrically located relative to the centre line CL and it is adapted to cooperate with an outer end portion 37 of the tube member 29 for closing the hole 22 in a closing position E shown with solid lines in FIG. 1. By rotating the closing device 23, i.e. here the wall 30, about the centre line CL, e.g. by means of a handle 38, the closing portion 35 is moved from its closing position E to an opening position F illustrated with broken lines in FIG. 2, whereby the the hole 22 is opened.

A longitudinal space 39 defined between the cylindrical walls 7 and the outer walls 32 may be open towards the surroundings.

In FIGS. 4 and 5 there is illustrated a mixing device 2 in the form of a bone cement syringe or sprayer 40 constructed as in e.g. U.S. Pat. No. 5,328,262. This bone cement syringe 40 is used for producing bone cement 3 which is then discharged by affecting the piston 9 with a discharge device (not shown). To the extent the mixing devices 1 and 2 have members with the same function, the same reference numerals have been used therefor. The bone cement syringe 40 preferably also has the filter 41 for preventing obstruction of at least one suction passage 42 through which the mixing space 6 and the vacuum source 19 are connected with each other.

Instead of being provided on the mixing device 2, the throttle and closing devices 20, 23 can be located at a base device 43, e.g. a plastic bowl or similar, and the mixing device 2 can be brought to cooperate therewith by being located on the base device 43. In FIGS. 4 and 5, the throttle and closing devices 20, 23 are only schematically illustrated.

As an alternative to the abovementioned embodiments, only the throttle device 20 is located on a mixing device 1 or 2, while the closing device 23 is mounted on a base device 43 or another suitable device, and the throttle and closing devices 20, 23 can be brought to cooperate with each other by locating the mixing device 1 or 2 in a suitable manner on or at the base device 43 or similar in order to bring the piston 9 to cooperate with the throttle and closing devices 20, 23 or the throttle device 20 to cooperate with the closing device 23.

As an example of the size of the mixing space 6 it should be mentioned that it can be dimensioned for production of 70-90 g, preferably about 60 g, bone cement 3, but it can of course be dimensioned for production of other amounts of bone cement 3.

The invention is not limited to the embodiments described above, but may vary within the scope of the subsequent claims. As an example not described in detail, the piston and/or the wall-like member 24 can be provided with spacing members 44 which are provided for determining the height of the intermediate space 21. The piston 9 may as an alternative to the abovementioned retention in the start position A be retainable therein by other means and may e.g. be released as defined in said U.S. Pat. No. 5,328,262.

The invention claimed is:

1. A mixing device for producing bone cement comprising:
   a mixing space (6) for mixing components (4, 5), said mixing space (6) including at least one piston (9) which can be brought to remain in a start position (A) at or adjacent a first end portion (8) of said mixing space (6) during mixing and which is releasable therefrom after mixing, said piston (9), after being released, being sucked towards a second end portion (10) of the mixing space (6) by a vacuum prevailing therein, and
   at least one throttle device (20) and
   a closing device (23),
   wherein the throttle device (20) and the piston (9) define an intermediate space (21), the closing device (23) and the throttle device (20) define an outer space (33), and the intermediate space (21) communicates with the surroundings through the outer space (33),
   wherein the throttle device (20) can be closed by the closing device (23) for air-tight isolation of the piston (9) from the surroundings in order to bring the piston to remain in the start position (A) during mixing,
   wherein the throttle device (20) is opened to release the piston (9) from the start position (A) and by generating a pressure drop between the air pressure in the surroundings and the piston, preventing full power affection thereof by said air pressure after said piston is released.

2. Mixing device according to claim 1, wherein the throttle device (20) is provided to generate such a pressure drop that the air pressure is prevented from imparting to the piston (9) such an unfavourably high speed during movement or displacement thereof.

3. Mixing device according to claim 1, wherein the throttle device (20) can be closed after the piston (9) has been moved or displaced to an inner position (A2).

4. Mixing device according to claim 1, wherein the throttle device (20) has a restriction in the form of at least one hole (22), and that the least cross-sectional area of this hole (22) or all cross-sectional areas of these holes is substantially less than the area of an outer side (9a) of the piston (9).

5. Mixing device according to claim 4, wherein the restriction comprises a plurality of holes (22), the cumulative cross-sectional area of the holes (22) being substantially less than the area of the outer side (9a) of the piston (9).

6. Mixing device according to claim 1, wherein the closing device (23) is movable relative to the throttle device (20) to close the throttle device (20).

7. Mixing device according to claim 1, wherein the closing device (23) is pivotally or rotatably mounted on the mixing device (1 or 2) for closing the throttle device (20).

8. Mixing device according to claim 1, wherein
   the throttle device (20) has a wall-like member (24) with at least one restriction in the form of a hole (22), and
   the closing device (23) comprising a closing portion (35) that closes or opens the hole (22).

9. Mixing device according to claim 1, wherein the mixing device (1 or 2) comprises a mixing means (12) which mixes the bone cement (3) in the mixing space (6).

10. Mixing device according to claim 1, wherein a vacuum source (19) is connected with the mixing space (6) or vice versa for generating the vacuum in said mixing space (6).

11. Mixing device according to claim 10, wherein the vacuum is generated in the mixing space (6) during mixing of the components (4, 5) as well as thereafter for sucking the piston (9) into the mixing space to collect the bone cement (3) in a part of the mixing space (6).

12. Mixing device according to claim 11, wherein the vacuum is generated in the mixing space (6) during mixing and collection such that the bone cement (3) is free or substantially free from entrapped air.

13. Mixing device according to claim 1, wherein
   the mixing device (1) comprises a cap (11) which can be removed for removal of the bone cement (3), and
   the mixing space (6) has such a diameter that one can remove the bone cement (3) therefrom by means of a spoon-like instrument.

14. Mixing device according to claim 1, wherein the mixing device (2) is designed as a bone cement syringe or sprayer (40) from which the bone cement (3) can be discharged by affecting the piston (9) in a discharge direction by means of a discharge device.

15. Mixing device according to claim 1, wherein the mixing device (1 or 2) comprises at least one filter (41) for preventing the bone cement (3) from obstructing suction passages (42) through which a vacuum source (19) can be connected with the mixing space (6) for generating the vacuum therein.

16. Mixing device according to claim 1, wherein the mixing space (6) of the mixing device (1 or 2) is dimensioned for producing 70-90 g of the bone cement (3).

17. Mixing device according to claim 1, wherein the vacuum in the mixing space (6) is within a range of 0.1-0.03 bar.

18. Mixing device according to claim 17, wherein the vacuum in the mixing space (6) is about 0.05 bar.

19. A mixing device for producing bone cement comprising:
   a wall defining a mixing space;
   a vacuum pump connected to the mixing space and generating a vacuum in the mixing space during mixing of components in the mixing space;
   at least one piston having a first position in the mixing space during mixing and a second position spaced from the first position, the at least one piston, after mixing, moving from the first position toward the second position under the influence of the vacuum;
   a throttle device fluidly connected with ambient air outside of the mixing space, the throttle device being opened to permit ambient air to apply pressure to the piston in order to release the piston from the first position, the throttle device generating a pressure drop between the ambient air and the piston to prevent the ambient air pressure from affecting the piston with full power after the piston is released from the first position; and
   a closing device,
   the throttle device and the piston defining an intermediate space, the closing device and the throttle device defining an outer space, and the intermediate space communicating with the surroundings through the outer space,
   the throttle device being closed by the closing device to isolate the piston air-tight from the surroundings in order to hold the piston in the first position during mixing.

* * * * *